(12) United States Patent
Tornier et al.

(10) Patent No.: US 10,610,363 B2
(45) Date of Patent: Apr. 7, 2020

(54) GLENOIDAL COMPONENT, SET OF SUCH COMPONENTS AND SHOULDER PROSTHESIS INCORPORATING SUCH A GLENOIDAL COMPONENT

(71) Applicant: Tornier SAS, Montbonnot Saint Martin (FR)

(72) Inventors: Alain Tornier, Saint Isnier (FR); Francois Sirveaux, Villers les Nancy (FR); Gilles Walch, Lyons (FR); Daniel Mole, Nancy (FR); Christophe Levigne, Caluire (FR); Pascal Boileau, Nice (FR); Luc Favard, Montlouis (FR)

(73) Assignee: Tornier SAS, Montbonnot Saint Martin (FR)

( * ) Notice: Subject to any disclaimer, the term of this patent is extended or adjusted under 35 U.S.C. 154(b) by 0 days.

(21) Appl. No.: 15/379,363

(22) Filed: Dec. 14, 2016

(65) Prior Publication Data

US 2017/0095336 A1 Apr. 6, 2017

Related U.S. Application Data

(63) Continuation of application No. 14/504,327, filed on Oct. 1, 2014, now Pat. No. 9,545,312, which is a (Continued)

(30) Foreign Application Priority Data

Jun. 15, 2004 (FR) ..................................... 04 06471

(51) Int. Cl.
*A61F 2/30* (2006.01)
*A61F 2/40* (2006.01)
(Continued)

(52) U.S. Cl.
CPC ........ *A61F 2/30734* (2013.01); *A61F 2/4081* (2013.01); *A61B 17/86* (2013.01);
(Continued)

(58) Field of Classification Search
CPC ............. A61F 2/30; A61F 2/3074; A61F 2/40
See application file for complete search history.

(56) References Cited

U.S. PATENT DOCUMENTS 3,694,820 A 10/1972 Scales et al.
3,815,157 A 6/1974 Skorecki et al.
(Continued)

FOREIGN PATENT DOCUMENTS

CH 426096 12/1966
CH 507704 5/1971
(Continued)

OTHER PUBLICATIONS

"Aequalis-Fracture Shoulder Prosthesis—Surgical Technique," Tornier, Inc., in 32 pages.
(Continued)

*Primary Examiner* — Bruce E Snow
(74) *Attorney, Agent, or Firm* — Knobbe Martens Olson & Bear, LLP

(57) ABSTRACT

This glenoidal component for a shoulder prosthesis comprises a base which may be immobilized on the glenoid cavity of a shoulder, and an element provided to be mounted on this base and forming a convex surface of articulation centred on an axis of symmetry. This axis of symmetry is non perpendicular to a rear face of the base intended to abut against the glenoid cavity, this making it possible to compensate a defect in parallelism between the resectioned surface of the glenoid cavity and the axis of the patient's spinal column.

(Continued)

A surgeon can select the component in which the axes of symmetry of the components are oriented differently with respect to their rear faces.

15 Claims, 5 Drawing Sheets

Related U.S. Application Data continuation of application No. 13/664,197, filed on Oct. 30, 2012, now Pat. No. 8,852,283, which is a continuation of application No. 11/147,177, filed on Jun. 8, 2005, now Pat. No. 8,303,665.

(60) Provisional application No. 60/579,284, filed on Jun. 15, 2004.

(51) Int. Cl.
*A61B 17/86* (2006.01)
*A61F 2/46* (2006.01)

(52) U.S. Cl.
CPC ............... *A61F 2/40* (2013.01); *A61F 2/4059* (2013.01); *A61F 2002/3023* (2013.01); *A61F 2002/3038* (2013.01); *A61F 2002/3079* (2013.01); *A61F 2002/30332* (2013.01); *A61F 2002/30433* (2013.01); *A61F 2002/30604* (2013.01); *A61F 2002/30616* (2013.01); *A61F 2002/30736* (2013.01); *A61F 2002/30785* (2013.01); *A61F 2002/30797* (2013.01); *A61F 2002/30878* (2013.01); *A61F 2002/4022* (2013.01); *A61F 2002/4062* (2013.01); *A61F 2002/4085* (2013.01); *A61F 2002/4638* (2013.01); *A61F 2220/0033* (2013.01); *A61F 2220/0041* (2013.01); *A61F 2230/0069* (2013.01); *A61F 2310/00011* (2013.01)

(56) References Cited

U.S. PATENT DOCUMENTS

| | | | |
|---|---|---|---|
| 3,842,442 A | 10/1974 | Kolbel | |
| 3,864,758 A | 2/1975 | Yakich | |
| 3,869,730 A | 3/1975 | Skobel | |
| 3,916,451 A | 11/1975 | Buechel et al. | |
| 3,978,528 A * | 9/1976 | Crep | A61F 2/40 623/19.12 |
| 3,979,778 A | 9/1976 | Stroot | |
| 3,992,726 A | 11/1976 | Freeman et al. | |
| 4,003,095 A | 1/1977 | Gristina | |
| 4,030,143 A | 6/1977 | Elloy et al. | |
| 4,040,131 A | 8/1977 | Gristina | |
| 4,054,955 A | 10/1977 | Seppo | |
| 4,135,517 A | 1/1979 | Reale | |
| 4,179,758 A | 12/1979 | Gristina | |
| 4,206,517 A | 6/1980 | Pappas et al. | |
| 4,261,062 A | 4/1981 | Amstutz et al. | |
| 4,550,450 A | 11/1985 | Kinnett | |
| 4,693,723 A | 9/1987 | Gabard | |
| 4,822,370 A | 4/1989 | Schelhas | |
| 4,846,840 A | 7/1989 | Leclercq et al. | |
| 4,865,605 A | 9/1989 | Dines et al. | |
| 4,865,609 A | 9/1989 | Roche | |
| 4,892,549 A | 1/1990 | Figgie, III et al. | |
| 4,919,670 A | 4/1990 | Dale et al. | |
| 4,957,510 A | 9/1990 | Cremascoli | |
| 4,963,155 A | 10/1990 | Lazerri et al. | |
| 4,986,833 A | 1/1991 | Worland | |
| 5,032,132 A | 7/1991 | Matsen, III et al. | |
| 5,080,673 A | 1/1992 | Burkhead et al. | |
| 5,080,685 A | 1/1992 | Bolesky et al. | |
| 5,127,920 A | 7/1992 | MacArthur | |
| 5,135,529 A | 8/1992 | Paxson et al. | |
| 5,152,797 A * | 10/1992 | Luckman | A61F 2/30734 623/20.16 |
| 5,163,961 A | 11/1992 | Harwin | |
| 5,171,289 A | 12/1992 | Tornier | |
| 5,181,928 A | 1/1993 | Bolesky et al. | |
| 5,192,329 A | 3/1993 | Christie et al. | |
| 5,201,882 A | 4/1993 | Paxson | |
| 5,206,925 A | 4/1993 | Nakazawa et al. | |
| 5,222,984 A | 6/1993 | Forte | |
| 5,226,915 A | 7/1993 | Bertin | |
| 5,261,914 A | 11/1993 | Warren | |
| 5,314,479 A | 5/1994 | Rockwood, Jr. et al. | |
| 5,314,485 A | 5/1994 | Judet | |
| 5,314,487 A | 5/1994 | Schryver et al. | |
| 5,326,359 A | 7/1994 | Oudard | |
| 5,330,531 A | 7/1994 | Cappana | |
| 5,358,526 A | 10/1994 | Tornier | |
| 5,383,936 A | 1/1995 | Kubein-Meesenburg et al. | |
| 5,405,399 A | 4/1995 | Tornier | |
| 5,425,779 A | 6/1995 | Schlosser et al. | |
| 5,429,639 A | 7/1995 | Judet | |
| 5,443,519 A | 8/1995 | Averill et al. | |
| 5,458,650 A | 10/1995 | Carret et al. | |
| 5,462,563 A | 10/1995 | Shearer et al. | |
| 5,505,731 A | 4/1996 | Tornier | |
| 5,507,817 A | 4/1996 | Craig et al. | |
| 5,507,818 A | 4/1996 | McLaughlin | |
| 5,507,824 A | 4/1996 | Lennox | |
| 5,531,793 A * | 7/1996 | Kelman | A61F 2/30724 606/60 |
| 5,549,682 A | 8/1996 | Roy | |
| 5,580,352 A | 12/1996 | Sekel | |
| 5,591,168 A | 1/1997 | Judet et al. | |
| 5,603,715 A | 2/1997 | Kessler | |
| 5,662,651 A | 9/1997 | Tornier et al. | |
| 5,676,702 A | 10/1997 | Ratron | |
| 5,702,447 A | 12/1997 | Walch et al. | |
| 5,702,457 A | 12/1997 | Walch et al. | |
| 5,702,478 A | 12/1997 | Tornier | |
| 5,702,486 A | 12/1997 | Craig et al. | |
| 5,723,018 A | 3/1998 | Cyprien et al. | |
| 5,728,161 A | 3/1998 | Camino et al. | |
| 5,741,335 A | 4/1998 | Gerber et al. | |
| 5,755,807 A | 5/1998 | Anstaett et al. | |
| 5,766,256 A | 6/1998 | Oudard et al. | |
| 5,800,551 A | 9/1998 | Williamson et al. | |
| 5,824,106 A | 10/1998 | Fournol | |
| 5,879,395 A | 3/1999 | Tornier et al. | |
| 5,879,405 A | 3/1999 | Ries et al. | |
| 5,902,340 A | 5/1999 | White et al. | |
| 5,910,171 A | 6/1999 | Kummer et al. | |
| 5,928,285 A | 7/1999 | Bigliani | |
| 5,944,758 A | 8/1999 | Mansat et al. | |
| 5,961,555 A | 10/1999 | Huebner | |
| 5,984,927 A | 11/1999 | Wenstrom, Jr. et al. | |
| 6,015,437 A | 1/2000 | Stossel | |
| 6,033,439 A | 3/2000 | Camino et al. | |
| 6,045,582 A | 4/2000 | Prybyla | |
| 6,045,583 A | 4/2000 | Gross et al. | |
| 6,102,953 A | 8/2000 | Huebner | |
| 6,129,764 A | 10/2000 | Servidio | |
| 6,162,254 A | 12/2000 | Timoteo | |
| 6,165,224 A | 12/2000 | Tornier | |
| 6,168,629 B1 | 1/2001 | Timoteo | |
| 6,171,341 B1 | 1/2001 | Boileau et al. | |
| 6,183,519 B1 | 2/2001 | Bonnin et al. | |
| 6,197,062 B1 | 3/2001 | Fenlin | |
| 6,197,063 B1 | 3/2001 | Dews | |
| 6,203,575 B1 | 3/2001 | Farey | |
| 6,206,925 B1 | 3/2001 | Tornier | |
| 6,228,120 B1 | 5/2001 | Leonard et al. | |
| 6,267,767 B1 | 7/2001 | Strobel et al. | |
| 6,283,999 B1 | 9/2001 | Rockwood, Jr. | |
| 6,299,646 B1 | 10/2001 | Chambat et al. | |
| 6,312,467 B1 | 11/2001 | McGee | |
| 6,328,758 B1 | 12/2001 | Tornier et al. | |
| 6,334,874 B1 | 1/2002 | Tornier et al. | |
| 6,358,250 B1 | 3/2002 | Orbay | |

(56) References Cited

U.S. PATENT DOCUMENTS

| | | |
|---|---|---|
| 6,364,910 B1 | 4/2002 | Schultz et al. |
| 6,368,352 B1 | 4/2002 | Camino et al. |
| 6,368,353 B1 | 4/2002 | Arcand |
| 6,379,387 B1 | 4/2002 | Tornier |
| 6,398,812 B1 | 6/2002 | Masini |
| 6,406,495 B1 | 6/2002 | Schoch |
| 6,406,496 B1 | 6/2002 | Rüter |
| 6,436,144 B1 | 8/2002 | Ahrens |
| 6,436,147 B1 | 8/2002 | Zweymuller |
| 6,454,809 B1 | 9/2002 | Tornier |
| 6,458,136 B1 | 10/2002 | Allard et al. |
| 6,475,243 B1 | 11/2002 | Sheldon et al. |
| 6,488,712 B1 | 12/2002 | Tornier et al. |
| 6,494,913 B1 | 12/2002 | Huebner |
| 6,506,214 B1 | 1/2003 | Gross |
| 6,508,840 B1 | 1/2003 | Rockwood, Jr. et al. |
| 6,514,287 B2 | 2/2003 | Ondrla et al. |
| 6,520,994 B2 | 2/2003 | Nogarin |
| 6,530,957 B1 | 3/2003 | Jack |
| 6,540,770 B1 | 4/2003 | Tornier et al. |
| 6,558,425 B2 | 5/2003 | Rockwood, Jr. |
| 6,569,202 B2 | 5/2003 | Whiteside |
| 6,582,469 B1 | 6/2003 | Tornier |
| 6,589,281 B2 | 7/2003 | Hyde, Jr. |
| 6,599,295 B1 | 7/2003 | Tornier et al. |
| 6,620,197 B2 | 9/2003 | Maroney et al. |
| 6,626,946 B1 | 9/2003 | Walch et al. |
| 6,673,114 B2 | 1/2004 | Hartdegen et al. |
| 6,673,115 B2 | 1/2004 | Resch et al. |
| 6,679,916 B1 | 1/2004 | Frankle et al. |
| 6,699,289 B2 | 3/2004 | Iannotti et al. |
| 6,736,851 B2 | 5/2004 | Maroney et al. |
| 6,746,487 B2 | 6/2004 | Scifert et al. |
| 6,749,637 B1 | 6/2004 | Bahler |
| 6,755,866 B2 | 6/2004 | Southworth |
| 6,761,740 B2 | 7/2004 | Tornier |
| 6,767,368 B2 | 7/2004 | Tornier |
| 6,780,190 B2 | 8/2004 | Maroney |
| 6,783,549 B1 | 8/2004 | Stone et al. |
| 6,790,234 B1 | 9/2004 | Frankle |
| 6,802,864 B2 | 10/2004 | Tornier |
| 6,824,567 B2 | 11/2004 | Tornier et al. |
| 6,863,690 B2 | 3/2005 | Ball et al. |
| 6,875,234 B2 | 4/2005 | Lipman et al. |
| 6,887,277 B2 | 5/2005 | Rauscher et al. |
| 6,890,357 B2 | 5/2005 | Tornier |
| 6,890,358 B2 | 5/2005 | Ball et al. |
| 6,942,699 B2 | 9/2005 | Stone et al. |
| 6,953,478 B2 | 10/2005 | Bouttens et al. |
| 6,969,406 B2 | 11/2005 | Tornier |
| 7,011,686 B2 | 3/2006 | Ball et al. |
| 7,033,396 B2 | 4/2006 | Tornier |
| 7,066,959 B2 | 6/2006 | Errico et al. |
| 7,108,719 B2 | 9/2006 | Horber |
| 7,166,132 B2 | 1/2007 | Callaway et al. |
| 7,169,184 B2 | 1/2007 | Dalla Pria |
| 7,175,663 B1 | 2/2007 | Stone |
| 7,195,645 B2 | 3/2007 | Disilvestro et al. |
| 7,238,207 B2 | 7/2007 | Blatter et al. |
| 7,238,208 B2 | 7/2007 | Camino et al. |
| 7,297,163 B2 | 11/2007 | Huebner |
| 7,309,360 B2 | 12/2007 | Tornier et al. |
| 7,329,284 B2 | 2/2008 | Maroney et al. |
| 7,338,498 B2 | 3/2008 | Long et al. |
| 7,338,528 B2 | 3/2008 | Stone et al. |
| 7,468,077 B2 | 12/2008 | Rochetin et al. |
| 7,544,211 B2 | 6/2009 | Rochetin et al. |
| 7,604,665 B2 | 10/2009 | Iannotti et al. |
| 7,666,522 B2 | 2/2010 | Justin et al. |
| 7,678,150 B2 | 3/2010 | Tornier |
| 7,753,959 B2 | 7/2010 | Berelsman et al. |
| 7,892,287 B2 | 2/2011 | Deffenbaugh |
| 8,002,839 B2 | 8/2011 | Rochetin et al. |
| 8,114,091 B2 | 2/2012 | Ratron et al. |
| 8,231,683 B2 | 7/2012 | Lappin et al. |
| 8,241,365 B2 | 8/2012 | Williams, Jr. et al. |
| 8,303,665 B2 * | 11/2012 | Tornier ................ A61F 2/4081 623/19.11 |
| 8,308,807 B2 | 11/2012 | Seebeck et al. |
| 8,465,548 B2 | 6/2013 | Long |
| 8,480,750 B2 | 7/2013 | Long |
| 8,532,806 B1 | 9/2013 | Masson |
| 8,632,597 B2 | 1/2014 | Lappin |
| 8,790,402 B2 | 7/2014 | Monaghan et al. |
| 8,852,283 B2 * | 10/2014 | Tornier ................ A61F 2/4081 623/19.11 |
| 8,864,834 B2 | 10/2014 | Boileau et al. |
| 8,961,611 B2 | 2/2015 | Long |
| 9,114,017 B2 | 8/2015 | Lappin |
| 9,351,844 B2 | 5/2016 | Walch et al. |
| 9,545,312 B2 * | 1/2017 | Tornier |
| 2001/0032021 A1 | 10/2001 | McKinnon |
| 2001/0047210 A1 | 11/2001 | Wolf |
| 2001/0049561 A1 | 12/2001 | Dews et al. |
| 2002/0032484 A1 | 3/2002 | Hyde, Jr. |
| 2002/0099381 A1 | 7/2002 | Maroney |
| 2002/0138148 A1 | 9/2002 | Hyde, Jr. |
| 2002/0143402 A1 | 10/2002 | Steinberg |
| 2002/0151982 A1 | 10/2002 | Masini |
| 2003/0009170 A1 | 1/2003 | Tornier |
| 2003/0009171 A1 | 1/2003 | Tornier |
| 2003/0028198 A1 | 2/2003 | Tornier et al. |
| 2003/0074072 A1 | 4/2003 | Errico et al. |
| 2003/0097183 A1 | 5/2003 | Rauscher et al. |
| 2003/0114933 A1 | 6/2003 | Bouttens et al. |
| 2003/0125809 A1 | 7/2003 | Iannotti et al. |
| 2003/0149485 A1 | 8/2003 | Tornier |
| 2003/0158605 A1 | 8/2003 | Tornier |
| 2004/0002765 A1 | 1/2004 | Maroney et al. |
| 2004/0006392 A1 | 1/2004 | Grusin et al. |
| 2004/0030394 A1 | 2/2004 | Horber |
| 2004/0034431 A1 | 2/2004 | Maroney et al. |
| 2004/0039449 A1 | 2/2004 | Tornier |
| 2004/0064189 A1 | 4/2004 | Maroney et al. |
| 2004/0064190 A1 | 4/2004 | Ball et al. |
| 2004/0133276 A1 | 7/2004 | Lang et al. |
| 2004/0134821 A1 | 7/2004 | Tornier |
| 2004/0138754 A1 | 7/2004 | Lang et al. |
| 2004/0148033 A1 | 7/2004 | Schroeder |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0210217 A1 | 10/2004 | Baynham et al. |
| 2004/0210317 A1 | 10/2004 | Maroney et al. |
| 2004/0215200 A1 | 10/2004 | Tornier et al. |
| 2004/0220673 A1 | 11/2004 | Pria |
| 2004/0220674 A1 | 11/2004 | Pria |
| 2004/0225367 A1 | 11/2004 | Glien et al. |
| 2004/0230197 A1 | 11/2004 | Tornier et al. |
| 2004/0210220 A1 | 12/2004 | Tornier |
| 2004/0267370 A1 | 12/2004 | Ondria |
| 2005/0008672 A1 | 1/2005 | Winterbottom et al. |
| 2005/0015154 A1 | 1/2005 | Lindsey et al. |
| 2005/0043805 A1 | 2/2005 | Chudik |
| 2005/0049709 A1 | 3/2005 | Tornier |
| 2005/0055102 A1 | 3/2005 | Tornier et al. |
| 2005/0065612 A1 | 3/2005 | Winslow |
| 2005/0085919 A1 | 4/2005 | Durand-Allen et al. |
| 2005/0085921 A1 | 4/2005 | Gupta et al. |
| 2005/0090902 A1 | 4/2005 | Masini |
| 2005/0107882 A1 | 5/2005 | Stone et al. |
| 2005/0113931 A1 | 5/2005 | Horber |
| 2005/0119531 A1 | 6/2005 | Sharratt |
| 2005/0143829 A1 | 6/2005 | Ondria et al. |
| 2005/0165490 A1 | 7/2005 | Tornier |
| 2005/0177241 A1 | 8/2005 | Angibaud et al. |
| 2005/0197708 A1 | 9/2005 | Stone et al. |
| 2005/0203536 A1 | 9/2005 | Laffargue et al. |
| 2005/0209700 A1 | 9/2005 | Rockwood et al. |
| 2005/0216092 A1 | 9/2005 | Marik et al. |
| 2005/0251263 A1 | 11/2005 | Forrer et al. |
| 2005/0256584 A1 | 11/2005 | Farrar |
| 2005/0267590 A1 | 12/2005 | Lee |
| 2005/0278031 A1 | 12/2005 | Tornier et al. |

(56) References Cited

U.S. PATENT DOCUMENTS

| | | |
|---|---|---|
| 2005/0278032 A1 | 12/2005 | Tornier et al. |
| 2005/0278033 A1 | 12/2005 | Tornier et al. |
| 2005/0288681 A1 | 12/2005 | Klotz et al. |
| 2005/0288791 A1 | 12/2005 | Tornier et al. |
| 2006/0004462 A1 | 1/2006 | Gupta |
| 2006/0009852 A1 | 1/2006 | Winslow et al. |
| 2006/0015185 A1 | 1/2006 | Chambat |
| 2006/0020344 A1 | 1/2006 | Schultz et al. |
| 2006/0030946 A1 | 2/2006 | Ball et al. |
| 2006/0074353 A1 | 4/2006 | Deffenbaugh et al. |
| 2006/0122705 A1 | 6/2006 | Morgan |
| 2006/0149388 A1 | 7/2006 | Smith et al. |
| 2006/0173457 A1 | 8/2006 | Tornier |
| 2006/0235538 A1 | 10/2006 | Rochetin et al. |
| 2006/0241775 A1 | 10/2006 | Buss |
| 2007/0016304 A1 | 1/2007 | Chudik |
| 2007/0142918 A1 | 6/2007 | Stone |
| 2007/0225817 A1 | 9/2007 | Reubelt et al. |
| 2007/0225818 A1 | 9/2007 | Reubelt et al. |
| 2007/0225821 A1 | 9/2007 | Reubelt et al. |
| 2007/0244564 A1 | 10/2007 | Ferrand et al. |
| 2007/0250174 A1 | 10/2007 | Tornier et al. |
| 2008/0195108 A1 | 8/2008 | Bhatnagar et al. |
| 2009/0149961 A1 | 6/2009 | Dallmann |
| 2010/0016975 A1 | 1/2010 | Iannotti et al. |
| 2010/0161066 A1 | 6/2010 | Iannotti et al. |
| 2010/0217399 A1 | 8/2010 | Groh |
| 2011/0190899 A1 | 8/2011 | Pierce et al. |
| 2013/0110470 A1 | 5/2013 | Vanasse et al. |
| 2013/0253656 A1 | 9/2013 | Long |
| 2013/0261752 A1 | 10/2013 | Lappin et al. |
| 2014/0142711 A1 | 5/2014 | Maroney et al. |
| 2014/0257499 A1 | 9/2014 | Winslow et al. |
| 2014/0371863 A1 | 12/2014 | Vanasse et al. |
| 2015/0150688 A1 | 6/2015 | Vanasse et al. |
| 2016/0242921 A1 | 8/2016 | Walch et al. |

FOREIGN PATENT DOCUMENTS

| | | |
|---|---|---|
| CN | 101340862 A | 1/2009 |
| DE | 19509037 C1 | 9/1996 |
| DE | 19630298 | 1/1998 |
| EP | 0299889 B1 | 1/1989 |
| EP | 0257359 B1 | 11/1991 |
| EP | 0524857 | 1/1993 |
| EP | 0617934 A1 | 10/1994 |
| EP | 0549480 B1 | 8/1997 |
| EP | 0599429 B1 | 10/1997 |
| EP | 0797964 A1 | 10/1997 |
| EP | 0679375 B1 | 9/1998 |
| EP | 0864306 A2 | 9/1998 |
| EP | 0712617 B1 | 9/1999 |
| EP | 0715836 B1 | 10/2001 |
| EP | 0664108 B1 | 8/2002 |
| EP | 0809986 B1 | 10/2002 |
| EP | 0927548 B1 | 5/2003 |
| EP | 0807426 B1 | 10/2003 |
| EP | 1380274 A1 | 1/2004 |
| EP | 1402854 B1 | 3/2004 |
| EP | 0903128 B1 | 5/2004 |
| EP | 1195149 B1 | 7/2005 |
| EP | 1064890 B1 | 9/2005 |
| EP | 1607067 A1 | 12/2005 |
| EP | 1062923 B9 | 7/2006 |
| EP | 1782765 A1 | 5/2007 |
| EP | 0903127 B1 | 6/2007 |
| EP | 1515758 B1 | 3/2009 |
| EP | 1639966 B1 | 9/2009 |
| EP | 1902689 B1 | 11/2011 |
| EP | 1996125 B1 | 5/2013 |
| EP | 2335655 B1 | 7/2013 |
| EP | 1973498 B1 | 4/2014 |
| EP | 1844737 B1 | 6/2015 |
| FR | 2248820 A1 | 5/1975 |
| FR | 2545352 | 11/1984 |
| FR | 2574283 | 6/1986 |
| FR | 2652498 | 4/1991 |
| FR | 2664809 | 1/1992 |
| FR | 2699400 | 6/1994 |
| FR | 2721200 | 12/1995 |
| FR | 2726994 | 5/1996 |
| FR | 2737107 | 1/1997 |
| FR | 2835425 | 8/2003 |
| FR | 2836039 | 8/2003 |
| FR | 2848099 A1 | 6/2004 |
| JP | 2009-513285 | 4/2009 |
| SU | 749392 | 7/1980 |
| WO | WO 91/07932 | 6/1991 |
| WO | WO 93/09733 | 5/1993 |
| WO | WO 96/17553 | 6/1996 |
| WO | WO 97/025943 | 7/1997 |
| WO | WO 98/46172 | 10/1998 |
| WO | WO 99/49792 | 10/1999 |
| WO | WO 99/65413 | 12/1999 |
| WO | WO 00/15154 | 3/2000 |
| WO | WO 00/41653 | 7/2000 |
| WO | WO 01/47442 | 7/2001 |
| WO | WO 02/039931 | 5/2002 |
| WO | WO 02/039933 | 5/2002 |
| WO | WO 02/067821 | 9/2002 |
| WO | WO 03/005933 | 1/2003 |
| WO | WO 03/094806 | 11/2003 |
| WO | WO 03/101320 | 12/2003 |
| WO | WO 07/109291 | 9/2007 |
| WO | WO 07/109319 | 9/2007 |
| WO | WO 07/109340 | 9/2007 |
| WO | WO 2015/068035 | 5/2015 |

OTHER PUBLICATIONS

"Aequalis-Fracture Suture Technique in 5 Steps," Tornier, Inc., in 2 pages.
"Aequalis-Glenoid Keeled and Pegged—Surgical Technique," Tornier, Inc. in 12 pages.
"Aequalis-Reversed™ Shoulder Prosthesis, Surgical Technique," Tornier, Inc., in 24 pages.
"Anatomic Glenoid, Surgical Technique," Smith & Nephew, Inc., Feb. 2000 in 6 pages.
"Anatomical Shoulder™—Cemented Shoulder Prosthesis Product Information and Surgical Technique," Sulzer Medica, 2000, in 30 pages.
"Anatomical Shoulder™ System—The new removable head option," Zimmer Inc., 2004 in 6 pages.
"Anatomical Shoulder™ System Surgical Technique—Removable head option for improved surgical results," Zimmer, Inc., 2004, in 33 pages.
Apoil, A., "A Condyle for the Rotator Cuff Muscles: The Total Shoulder Prosthesis," Aesculap—ICP S.A., Feb. 1994, in 4 pages.
Bigliani/Flatow®—The Complete Shoulder Solution, Designed by Shoulder Surgeons for Shoulder Surgery, Zimmer, Inc., 2001 in 6 pages.
"Bigliani/Flatow®—The Complete Shoulder Solution, Total Shoulder Arthroplasty Surgical Technique," Zimmer, Inc., 2003, in 30 pages.
Bigliani/Flatow®—The Complete Shoulder Solution, 4-Part Fracture of the Humerus Surgical Technique, Zimmer, Inc., 2001.
"Bio-Modular® / Bi-Polar Shoulder Arthroplasty," Biomet, Inc., 1997, in 2 pages.
"Bio-Modular® Choice—Shoulder System—Surgical Technique," Biomet Orthopedics, Inc., 2004, in 16 pages.
Boileau, P., et al. "Adaptability and modularity of shoulder prosthese," Maitrise Orthopédique, https://www.maitriseorthop.com/corpusmaitri/orthopaedic/prothese_epaule_orthop/boileau_us.shtml, downloaded Jan. 3, 2006.
Boileau, P., et al. "Arthroscopic Repair of Full-Thickness Tears of the Supraspinatus: Does the Tendon Really Heal?" The Journal of Bone and Joint Surgery, Inc., Jun. 2005, 87A(6): 1229-1240.
Boileau, P., "Technique de synthèse des tubérosités," Tornier, Inc., 2005, in 2 pages.

(56) References Cited

OTHER PUBLICATIONS

Buechel, F.F., "Buechel-Pappas™ Modular Salvage Shoulder System, Surgical Procedure," Endotec, Inc., Aug. 2001, in 8 pages.
Buechel, F.F., "Buechel-Pappas™ Resurfacing Shoulder System, Surgical Procedure" Endotec, Inc., Aug. 2000, in 8 pages.
Buechel, F.F., "Buechel-Pappas™ Total Shoulder System, Surgical Procedure," Endotec, Inc., Aug. 2000, in 16 pages.
Cofield, R.H., "Cofield² Total Shoulder System, Surgical Technique," Smith & Nephew, 1997, in 32 pages.
"Copeland™ Humeral Resurfacing Head," Biomet Orthopedics, Inc., 2001, in 12 pages.
"Delta CTA™ Reverse Shoulder Prosthesis—Surgical Technique," DePuy International Ltd., revised Aug. 2004, in 28 pages.
"Design Rationale," Latitude® Total Elbow, pp. 3-38.
"FDA Summary of Safety and Effectiveness: Glenoid Component for the Foundation™ Total Shoulder System," Encore Orthopedics, Inc., Apr. 15, 1996, in 1 page.
Fenlin, Jr., J.M., "Total Glenohumeral Joint Replacement," Symposium on Surgery of the Shoulder, Orthopedic Clinics of North America, Apr. 1975, 6(2): 565-583.
"Global C.A.P.™ Surgical Technique, Resurfacing Humeral Head Implant," DePuy International, Ltd., revised Oct. 2004, in 23 pages.
Hertel, R., "Technical considerations for implantation of EPOCA glenoid components (Leseprobe)," Epoca Newsletter, May 14, 2001, in 1 page.
International Search Report from international application No. PCT/US2006/035920, dated Dec. 28, 2006, 7 pp.
Klein, T.J., et al., "Mechanically Favorable Bone Remodeling in Rotator Cuff Arthropathy Patients with Good Function," Minneapolis Sports Medicine Center and University of Minnesota, in 2 pages.
Mansat, M., "Neer 3™, Surgical Technique for Fractures," Smith & Nephew, Sep. 2000, in 19 pages.
Nicholson, G.P., "Chapter 7: Arthroplasty and Rotator Cuff Deficiency," Shoulder Arthroplasty, 2005, pp. 149-166.
"Offset Head: Bio-Modular® Total Shoulder," Biomet, Inc. 2000 in 2 pages.
"The Foundation® Total Shoulder System," Encore Surgical, in 2 pages.
"The Townley Modular Shoulder—Design by Reason," Biopro, Inc., in 2 pages.
"Tornier Aequalis® Reversed Shoulder G2 Baseplate," Tornier, Inc., Oct. 8, 2005.
"Tornier Aequalis® Reversed 2 Prong Capsular Retractor, "Tornier, Inc., Oct. 8, 2005.
"Tornier Surgical Technique Addendum, Tornier Aequalis® Reversed Hemi-Adaptor Technique," Tornier, Inc., Aug. 8, 2005.
"Tornier Surgical Technique Addendum, Aequalis® Reversed Shoulder Polyethylene Insert," Tornier, Inc., Oct. 8, 2005, in 1 page.
"Zimmer® Shoulder Retractors," Zimmer, Inc., 2000, in 2 pages.

\* cited by examiner

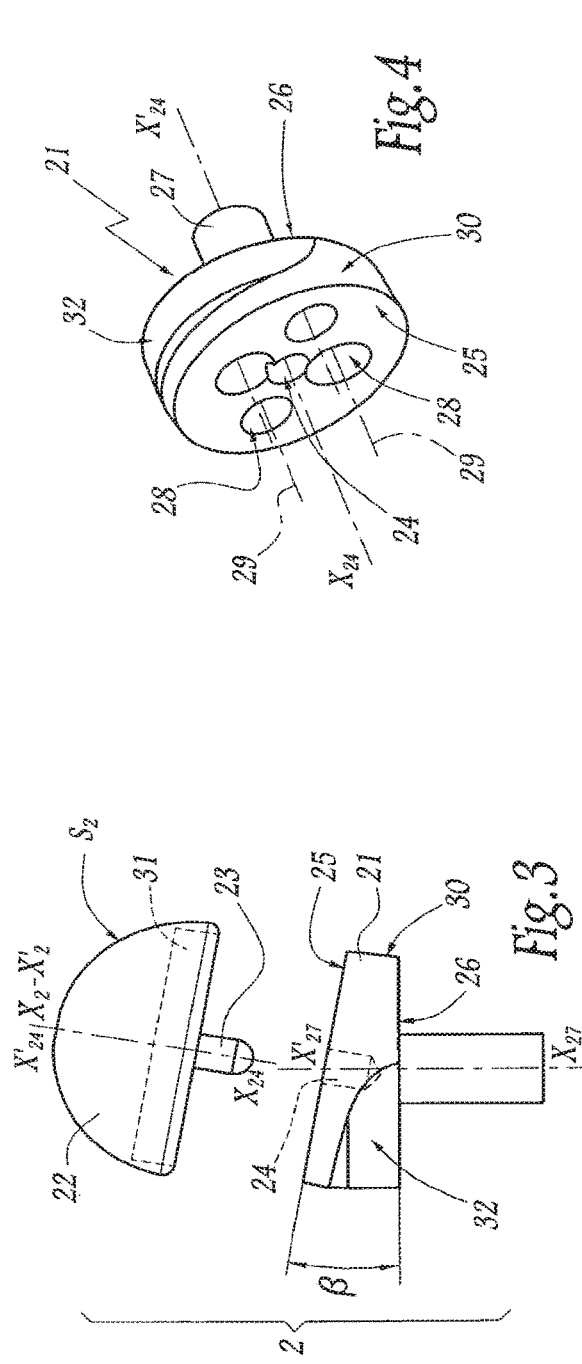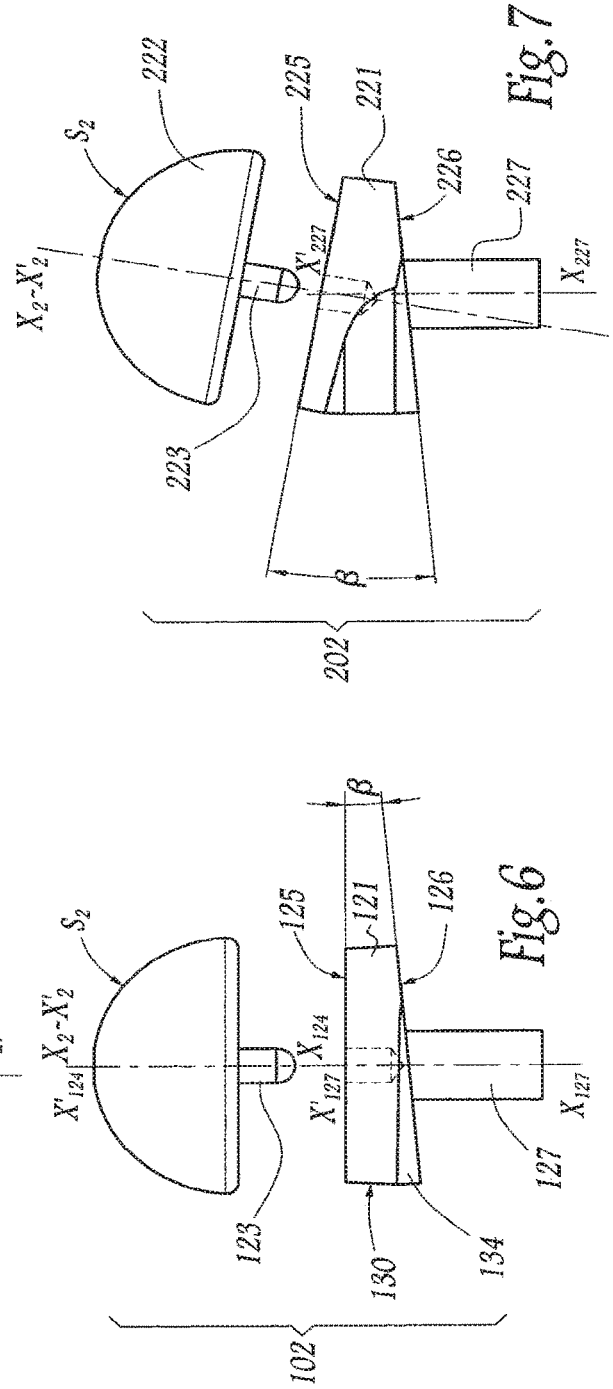

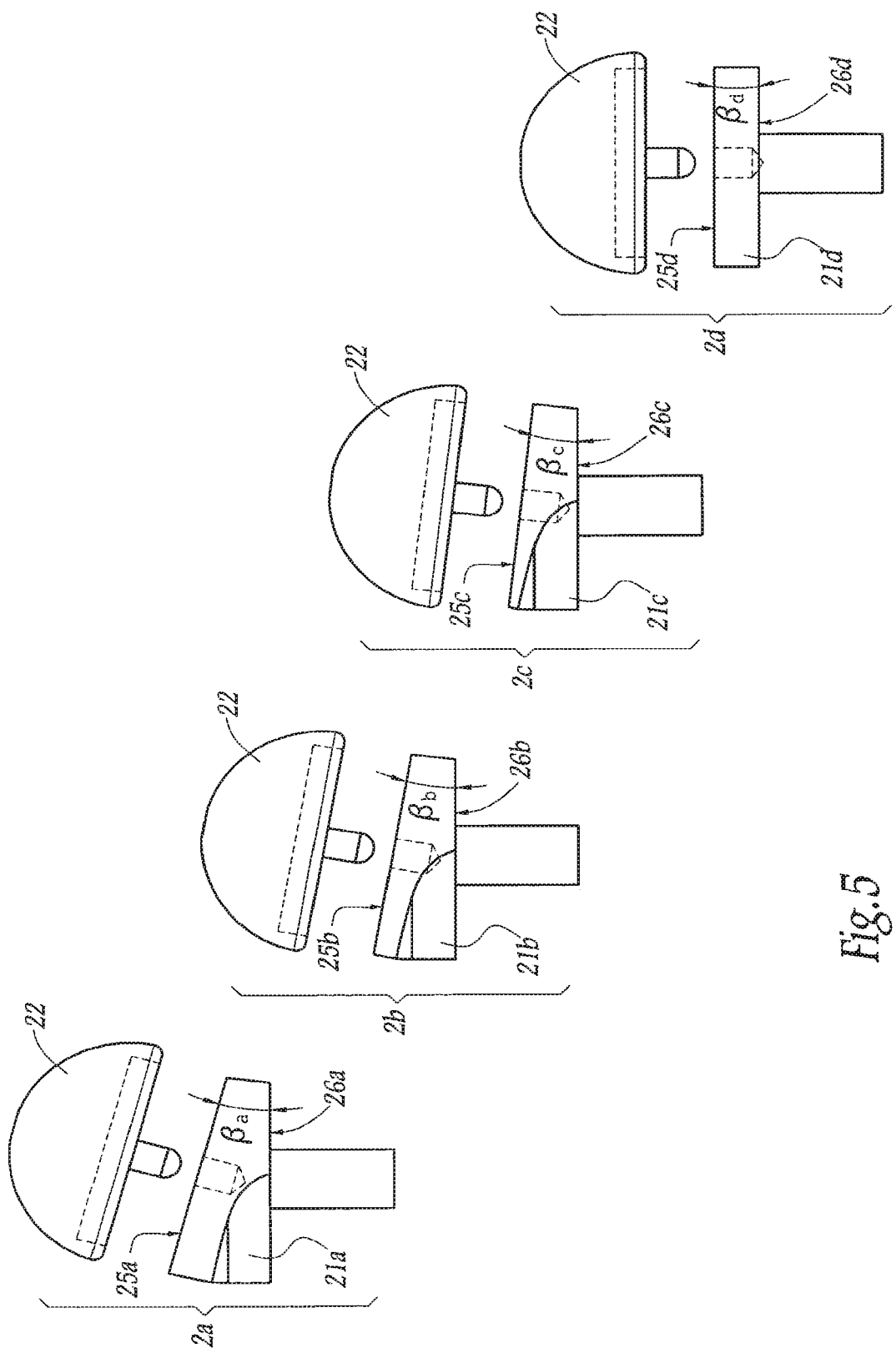

GLENOIDAL COMPONENT, SET OF SUCH COMPONENTS AND SHOULDER PROSTHESIS INCORPORATING SUCH A GLENOIDAL COMPONENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

FIELD OF THE INVENTION

The present invention relates to a glenoidal component of a shoulder prosthesis and to a set of such components that may be used for constituting a prosthesis. The invention also relates to a shoulder prosthesis comprising such a 5 component as well as to a method for installing such a component.

BACKGROUND OF THE INVENTION

In the domain of shoulder protheses, it is known, for example from U.S. Pat. No. 3,978,528, to constitute a so-called "inverted" prosthesis in which a convex articular surface fast with the glenoid cavity and a concave articular surface fast with the humerus, cooperate in order to recreate a joint at the level of the shoulder. In this type of prosthesis, the glenoidal component may be formed, as disclosed in FR-A-2 835 425, by a base intended to be immobilized on the glenoid cavity and by an element intended to be mounted on this base and defining the convex surface of articulation.

Furthermore, it is known from FR-A-2 836 039, to provide a possibility of mounting an element forming a convex surface of articulation on a corresponding base in different positions, this allowing an adjustment of the articular surface in height with respect to the glenoid cavity.

The base of the known glenoidal components is provided with a so-called "rear face" intended to abut against a resectioned surface of the glenoid cavity which is normally substantially vertical when the patient is in standing position. Now, it may happen that the upper part of the scapula be worn out or destroyed, to the point of modifying the kinematics of the implant by the displacement of the original centre of rotation, this having for consequence to limit the movements of the patient's arm.

It is a particular object of the present invention to overcome these drawbacks by proposing a glenoidal component which ensures a correct positioning of the convex surface of articulation, including when the glenoid cavity is damaged or worn out in its upper part and even in its lower part.

SUMMARY OF THE INVENTION

In that spirit, the invention relates to a glenoidal component of a shoulder prosthesis which forms a convex surface of articulation centred on an axis of symmetry. This component is characterized in that the axis of symmetry of the convex surface of articulation is non perpendicular to a rear face of the component which is intended to abut against the glenoid cavity.

Thanks to the invention, the convex surface of articulation may be inclined downwardly or "slanted" with respect to the rear face of the component, this making it possible to orient this articular surface correctly, including when the bearing surface created in the glenoid cavity by resection is not parallel to the direction of the patient's spinal column. The invention therefore makes it possible to "compensate" a defect in parallelism between the resectioned surface of the glenoid cavity and the axis of the patient's spinal column.

According to advantageous but non-obligatory aspects, a glenoidal component may incorporate one or more of the following characteristics taken in any technically admissible combination:

In assembled configuration of the component and when the rear face is 20 vertical, the axis of symmetry of the convex surface of articulation is directed downwardly, moving away from the rear face.

The component comprises a base adapted to be immobilized on the glenoid cavity of a shoulder and an element provided to be mounted on this base and defining the convex articular surface, while the base is provided with a substantially planar front face in which is pierced a housing for receiving a finger for centring the element forming the convex surface of articulation, this housing being centred on an axis substantially perpendicular to this front face, this front face not being parallel to the rear face of the base. In that case, the front and rear faces of the base may together form an angle included between 2° and 18°. The base may be provided with an axisymmetric surface centred on an axis perpendicular to its front face, this surface being adapted to cooperate with an internal surface of the afore-mentioned element for centring and immobilization thereof on the base.

The component may be provided with an anchoring stem which extends in a direction which is not perpendicular to at least a part of its rear face.

The component comprises a base adapted to be immobilized on the glenoid cavity of a shoulder and an element provided to be mounted on this base and defining the convex articular surface, while the element which forms the convex surface of articulation is provided with a skirt which is non-symmetrical with respect to the axis of the afore-mentioned surface, which extends this surface and in which is defined, at least in part, a housing for receiving at least a part of the base. This skirt may be substantially in the form of a portion of torus. The element which defines the convex surface of articulation is advantageously provided with a bore for passage of a member for manoeuvring a means for connecting this element on the base, this passage extending substantially in a direction globally perpendicular to this surface but not merged with its axis of symmetry.

The Invention also relates to a set of glenoidal components for a shoulder prosthesis of the type defined hereinabove which allows a surgeon to select a component of appropriate geometry as a function of the effective configuration of the glenoid cavity once the latter is resectioned. This set of components is characterized in that the orientation of the axis of symmetry of the convex surface of articulation, with respect to a rear face of each component intended to abut against the glenoid cavity, is variable from one component to another.

According to a first variant embodiment, the front and rear faces of the bases of the components are not necessarily parallel to each other, in which case the angle between these front and rear faces is different from one component to another.

According to another variant, the elements of these components which form a convex articular surface may each be provided with a skirt, as mentioned hereinabove, the dimensions of the skirts being different from one component to another.

The invention also relates to a total shoulder prosthesis which comprises a 10 glenoidal component as described hereinabove or selected from a set of components as described hereinabove.

Finally, the invention relates to a method for installing a glenoidal component of a total shoulder prosthesis, such a component defining a convex articular surface centred on an axis of symmetry, this method comprising steps 15 consisting in:

milling the patient's glenoid cavity in order to create a bearing surface for the component, selecting, from a plurality of glenoidal components of which the axes of symmetry of the convex articular surfaces are oriented differently with respect to their bearing face against the resectioned surface of the glenoid cavity, a component which may be applied against this surface in such a position that the afore-mentioned axis of symmetry is globally perpendicular to the direction of the patient's spinal column, and immobilizing the selected glenoidal component on the glenoid cavity in 25 the afore-mentioned position.

BRIEF DESCRIPTION OF THE DRAWINGS

The invention will be more readily understood and other advantages thereof will appear more clearly in the light of the following description of five forms of embodiment of a glenoidal component and of two forms of embodiment of a set of glenoidal components in accordance with its principle, given solely by way of example and made with reference to the accompanying drawings, in which:

FIG. 3 is an exploded side view of the glenoidal component used in the prosthesis of FIG. 2.

FIG. 4 is a view in perspective of a base belonging to the component 15 shown in FIG. 3.

FIG. 5 schematically shows a set of glenoidal components incorporating the one shown in FIGS. 3 and 4.

FIG. 6 is a view similar to FIG. 3 for a component in accordance with a second form of embodiment of the invention.

FIG. 7 is a view similar to FIG. 3 for a component in accordance with a third form of embodiment of the invention.

DETAILED DESCRIPTION OF THE PREFERRED EMBODIMENT

Figure 1:
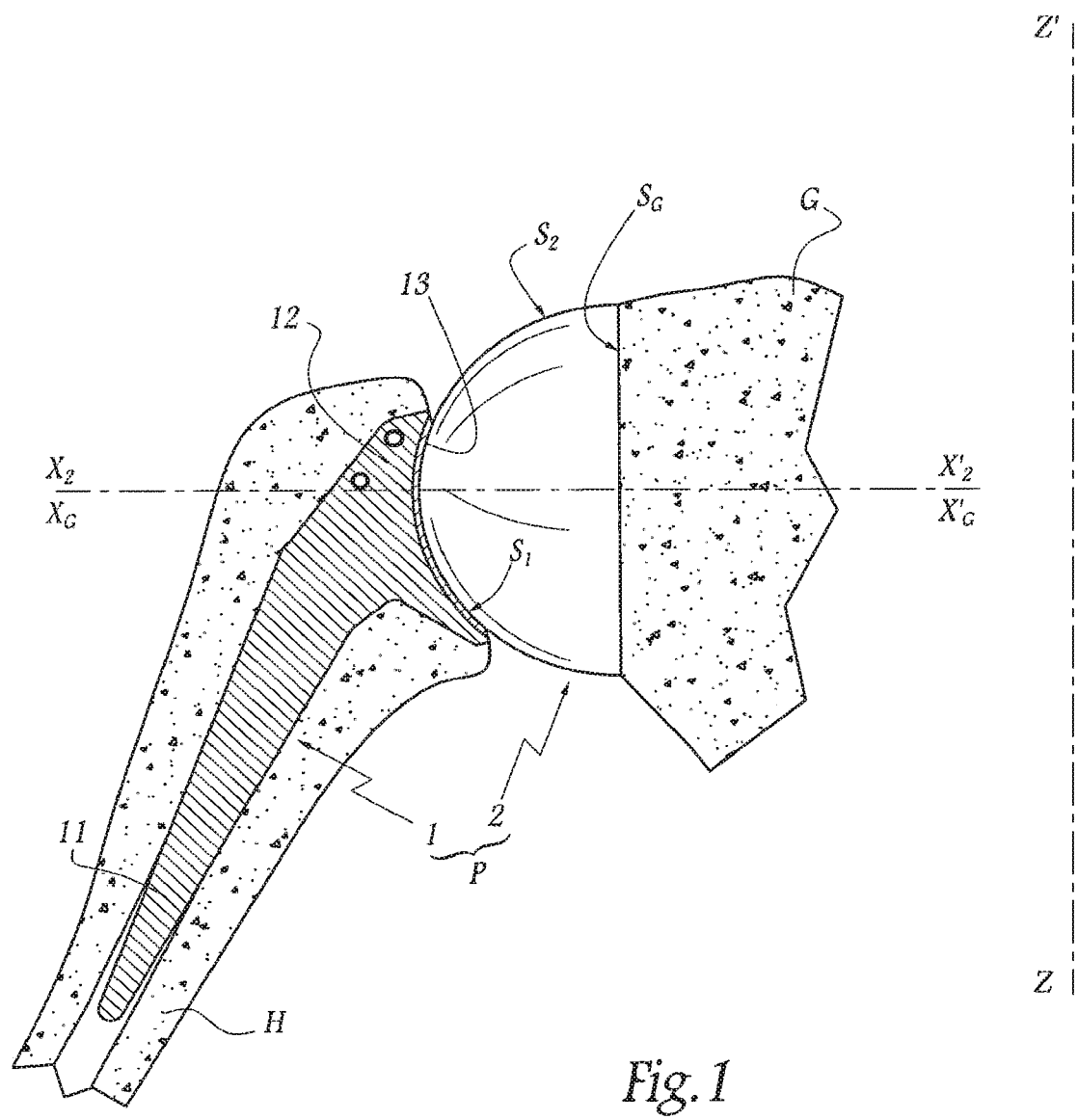
FIG. 1 schematically shows a shoulder prosthesis according to the. invention implanted on a patient in a first configuration.

Referring now to the drawings, the prosthesis P shown in FIG. 1 comprises a humeral component 1 composed of a stem 11 intended to be anchored in the medullary canal of the humerus H, as well as of a metaphyseal part 12 in which is immobilized a cup 13 made of polyethylene defining a concave articular surface $S_1$ substantially in the form of a portion of sphere.

In accordance with a variant of the invention (not shown), the component I does not present a cup 13, the surface S1 being formed by the metaphyseal part which is made of metal.

The prosthesis P also comprises a glenoidal component 2 which defines a convex articular surface $S_2$ substantially in the form of a hemisphere.

In order to render the drawing clearer, the component 1 is shown in section, while the component 2 is shown in an outside view in FIG. 1.

The surface $S_2$ is substantially in the form of a hemisphere and $X_2$-$X'_2$ denotes the axis of symmetry on which this surface is centred.

Furthermore, Z-Z' denotes a vertical axis passing through the centre of the spinal column of a patient who is standing up.

$S_G$ denotes the milled surface of the glenoid cavity G against which the component 2 abuts when it is mounted on the glenoid cavity.

Normally, the surface $S_G$ is substantially parallel to axis Z-Z', with the result that an axis $X_G$-$X'_G$ normal to the surface $S_G$ and passing through its centre, is substantially perpendicular to axis Z-Z', i.e. substantially horizontal when the patient is standing up. In the configuration of FIG. 1 which corresponds to a nominal configuration of implantation, axes $X_G$-$X'_G$ and $X_2$-$X'_2$ merge and are both horizontal.

Figure 2:
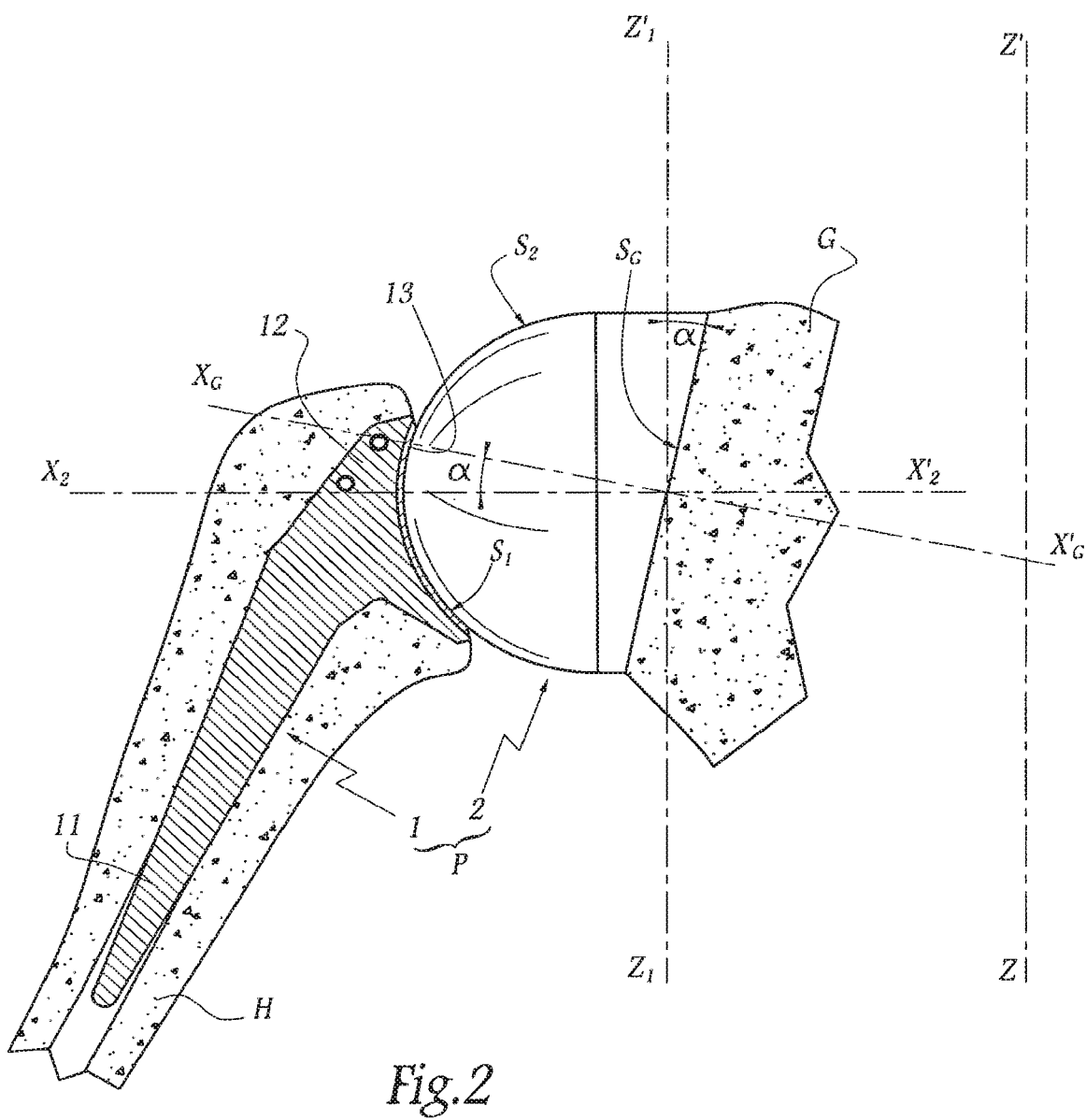
FIG. 2 is a view similar to FIG. 1 for a prosthesis likewise according to the invention, implanted in a second configuration.

However, as shown in FIG. 2, it may happen that the surface $S_G$ is not really parallel to the axis Z-Z', particularly due to wear of the glenoid cavity G or a partial destruction thereof in its upper part, and even its lower part. In that case, the surface $S_G$ forms a non-zero angle a with respect to a straight line $Z_1$-$Z'_1$ parallel to axis Z-Z' and passing through the centre $M_G$ of the surface $S_G$. When the patient is standing up, the axis $X_G$-$X'_G$ forms the same angle a with respect to the horizontal.

According to the invention, the component 2 is configured so that the axis $X_2$-$X'_2$ of the surface $S_2$ is substantially horizontal when the patient is standing up, despite the non-optimal orientation of the surface $S_G$.

The component 2 is shown in exploded side view in FIG. 3 and comprises a base or plate 21 intended to be fixed on the glenoid cavity G; as well as a metallic element 22, sometimes called "head", which defines the surface $S_2$ and which is provided with a centring finger 23 intended to penetrate in a housing 24 made in the base 21 and centred on an axis $X_{24}$-$X'_{24}$ perpendicular to the front face 25 of the base 21 which is substantially planar and oriented opposite the glenoid cavity when the base is mounted on the glenoid cavity.

26 denotes the rear face of the base 21 which bears against the surface $S_G$ when the base is in mounted configuration.

An anchoring stem 27 extends from the surface 26 in a direction parallel to an axis $X_{27}$-$X'_{27}$ perpendicular to the surface 26.

The base 21 is also pierced with four orifices 28 for passage of four screws 29 represented solely by their lines of axis in FIG. 4.

The front face 25 is in the form of a disc centred on the axis $X_{24}$-$X'_{24}$ and bordered by a truncated surface 30, centred on the axis $X_{24}$-$X'_{24}$ and convergent opposite the stem 27.

The surface 30 extends all around the front face 25 but joins the rear face 26 over only a part of the periphery of the base 21.

The face 26 is substantially planar and the faces 25 and 26 are not parallel to each other. β denotes the non-zero angle formed between the faces 25 and 26.

The inclined character of the front face 25 with respect to the rear face 26 of the base 21 makes it possible to "compensate" completely or partially the inclined character with respect to the straight line $Z_1$-$Z'_1$ of the surface $S_G$, as long as the least thick part of the base 21, which is shown to the right of FIG. 3, is disposed in the vicinity of the lower part of the surface $S_G$, i.e. the part located towards the patient's ribs.

When the base or plate 21 has been anchored on the glenoid cavity G as indicated hereinabove thanks to the stem 27 and to the positioning of the four screws 29, the element 22 may be placed in position by introducing the finger 23 in the housing 24 and causing an internal surface 31 of the element 22 shown in broken lines only in FIG. 3, to bear against the surface 30. The geometries of the surfaces 30 and 31 are adapted to obtain a locking in the manner of a Morse cone.

In this way, the relative orientation of the faces 25 and 26 makes it possible to orient the axis $X_2$-$X'_2$ of the surface $S_2$ downwardly in FIG. 2 with respect to axis $X_G$-$X'_G$ in its part which projects beyond the glenoid cavity, i.e. to return this axis into substantially horizontal configuration, while the surface $S_G$ is not parallel to axis Z-Z'.

Taking into account the relative orientation of the faces 25 and 26, the surface 30 borders the face 25 only over a fraction of the height of that part of the based located between the faces 25 and 26. 32 denotes the portion of peripheral surface of the base 21 which is not formed by part 30. This surface is out of true.

As is more particularly visible in FIG. 5, a set of glenoidal components according to the invention may incorporate a plurality of glenoidal components 2a, 2b, 2c and 2d of which the bases 21a, 21b, 21c and 21d have front faces 25a, 25b, 25c and 25d which make different angles βa, βb, βc and βd with respect to their respective rear faces 26a, 26b, 26c and 26d. It will be noted that the front and rear faces of the base 21d are substantially parallel, the angle βd between them being, in that case, zero.

The element 22 associated with each base 21a, 21b, 21c and 21d may be the same or be different from one component to another.

In this way, when a surgeon installs a shoulder prosthesis P, he may, as a function of the relative orientation of the surface $S_G$ and of the axis Z-Z', select a glenoidal component of which the base comprises front and rear faces oriented in such a manner as to allow the main part of the defect of orientation of the surface $S_G$ to be compensated.

Of course, the number of glenoidal components of a set such as the one shown in FIG. 5 is not necessarily four. It may be chosen as a function of the desired precision. In addition, it is not compulsory that, in such a set, a plate has surfaces which are parallel to each other, as shown to the right in FIG. 5. However, it is noted that the glenoidal component shown to the right of FIG. 5 may be used when the prosthesis P is to be implanted in the configuration of FIG. 1.

The installation of a total shoulder prosthesis is facilitated by the use of such a set of components insofar as the surgeon can select a glenoidal component effectively adapted to the patient's morphology, them immobilize this component in a position such that the axis of symmetry of the convex articular surface is substantially perpendicular to the longitudinal axis of the patient's spinal column.

In the second form of embodiment of the invention shown in FIG. 6, elements similar to those of the first embodiment bear identical references increased by 100. The glenoidal component 102 of this embodiment comprises an element 122 which bears a substantially hemispherical convex articular surface, this element being identical to that of the first embodiment. The base 121 of the component 102 also comprises an anchoring stem 127. This anchoring stem is centred on an axis $X_{27}$-$X'_{27}$ perpendicular to the front face 125 of the base 121 which is planar and bordered by a truncated surface 130. The base 121 is provided with a housing 124 for receiving a finger 123 belonging to the element 122, this finger being centred on the axis of symmetry $X_2$-$X'_2$ of the surface $S_2$. The central axis $X_{124}$-$X'_{124}$ of the housing 124 merges with the central axis $X_{127}$-$X'_{127}$ of the stem 127.

This form of embodiment differs from the preceding one in that the rear face 126 of the base 121 is not perpendicular to the axis $X_{127}$-$X'_{127}$, with the result that a non-zero angle β exists between the faces 125, and 126.

In this embodiment, it may be considered that the rear face 126 is provided with a "heel" or wedge 134 which serves to compensate the non-optimal orientation of the surface $S_G$.

In the third form of embodiment of the invention shown in FIG. 7, elements similar to those of the first embodiment bear identical references increased by 200. The glenoidal component 202 of this embodiment comprises a 25 base 221 as well as an element 222 which forms a substantially hemispherical articular surface S2 centred on an axis $X_2$-$X'_2$ on which a centring finger 223 is also centred.

The front (225) and rear (226) faces of the base 221 are not parallel to each other and define a non-zero angle β. This embodiment incorporates certain elements of the first and second embodiments, namely that the surfaces 225 and 226 are both inclined, in different directions, with respect to a longitudinal axis $X_{227}$-$X'_{227}$ of an anchoring stem 227 of the base 221 in the glenoid cavity.

Figure 9:
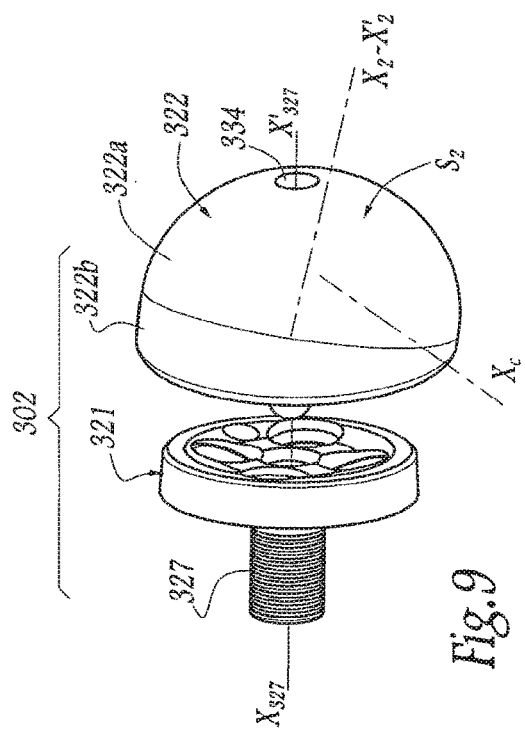
FIG. 9 is an exploded view in perspective of the component of FIG. 8.
Figure 11:
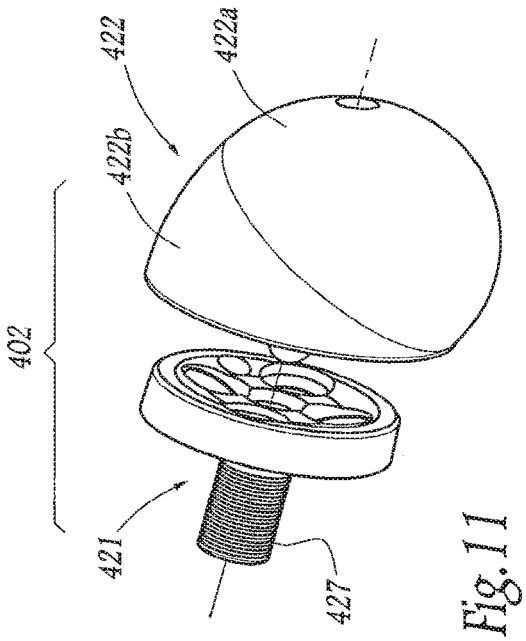
FIG. 11 is a view similar to FIG. 9 for the component of FIG. 10.
Figure 8:
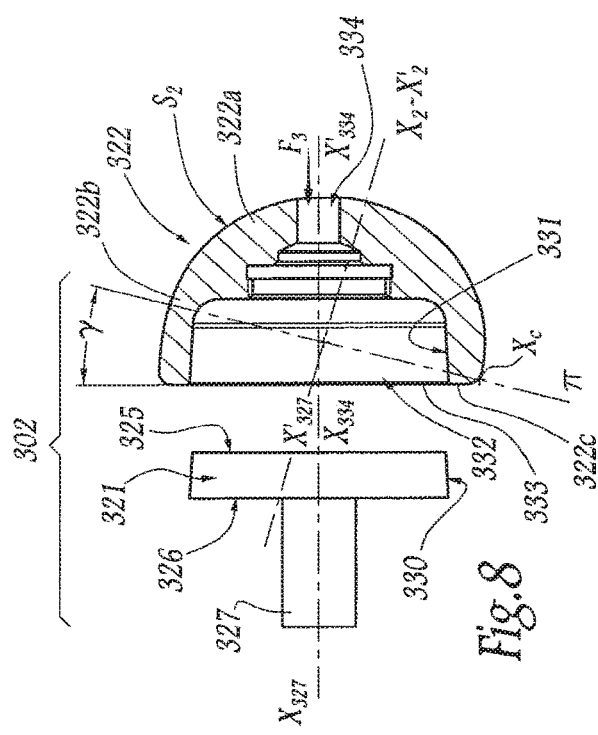
FIG. 8 shows a glenoidal component in accordance with a fourth form of embodiment of the invention of which the base is shown in side view and of which the element defining the convex articular surface is shown in cross section.

In the fourth form of embodiment of the invention shown in FIGS. 8 and 9, elements similar to those of the first embodiment bear identical references increased by 300. The glenoidal component 302 of this embodiment comprises a base 321 similar to that of the component shown to the right in FIG. 5, i.e. of which the front (325) and rear (326) faces are substantially parallel to each other and perpendicular to a central axis $X_{327}$-$X'_{327}$ of an anchoring stem 327.

An element 322 intended to be mounted on the base 321 defines a surface $S_2$ substantially in the form of a hemisphere and centred on an axis $X_2$-$X'_2$ which is not parallel to axis $X_{327}$-$X'_{327}$ when the element 322 is in mounted configuration on the base 321. To that end, the portion 322a of the element 322 which defines the surface $S_2$ is extended by a skirt 322b in the form of a portion of torus centred on an axis $X_c$ perpendicular to axis $X_2$-$X'_2$ and tangential to the convex articular surface S2 in the vicinity of a zone of intersection between this surface S2 and a plane 1t perpendicular to axis $X_2$-$X'_2$ and passing through the centre C2 of the surface $S_2$. γ denotes the angular amplitude of the skirt 322, i.e. the angle between the plane π and the rear face 322c of the element 322 intended to be turned towards the resectioned surface of the glenoid cavity when the component 302 is in mounted configuration.

A housing 332 is made inside the element 322, both in the skirt 322b and 25 in the portion 322a. This housing is intended to receive the part of the base 321 defined between the surfaces 325 and 326. The housing 332 is bordered by a truncated surface 331 convergent in the direction of the surface $S_2$, while a surface 330 of the same geometry is provided on the element 321 between the faces 325 and 326.

333 denotes the circular opening for entrance in the housing 332.

The surface $S_2$ is pierced with a passage 334 allowing the introduction of a tool in the direction of arrow $F_3$ up to the interior of the element 322, which makes it possible to manoeuvre a screw (not shown) for immobilizing the element 322 on the base 321. Such a screw may in particular control the displacement of a finger such as the finger 23 of the first embodiment, which is, in that case, threaded, in order to be meshed with a tapped part of the base 321, and this in accordance with the technical teaching of FR-A-2 835 425.

$X_{334}$-$X'_{334}$ denotes the longitudinal axis of the passage 334. This axis is perpendicular to the surface $S_2$ and offset by angle γ with respect to axis $X_2$-$X'_2$.

Figure 10:
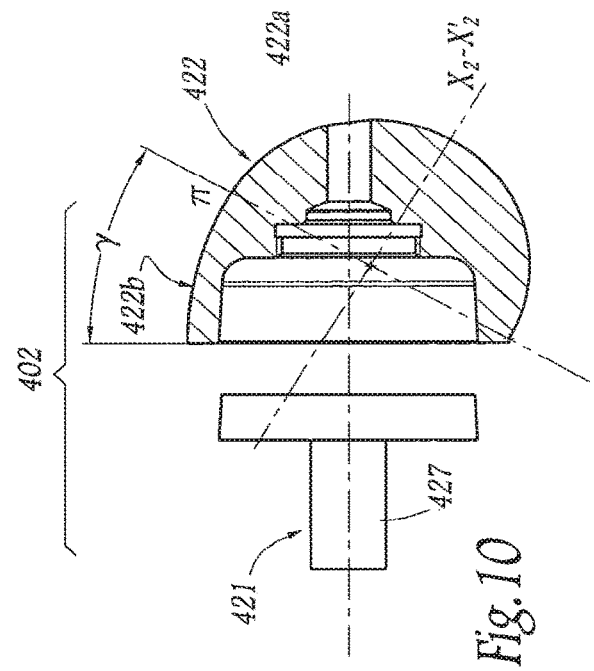
FIG. 10 is a view similar to FIG. 8 for a component in accordance with a fifth form of embodiment of the invention.

In the fifth form of embodiment of the invention shown in FIG. 10, elements similar to those of the first embodiment bear identical references increased by 400. The glenoidal component 402 of this embodiment is made in accordance with the same principle as that of the fourth embodiment, with a base 421 identical to base 321 and en element 422 which defines a surface $S_2$ centred on an axis $X_2$-$X'_2$ inclined downwardly in FIG. 10. This embodiment differs from the preceding one in that the angular amplitude γ of the skirt 422b, which extends the portion 422a of the element 422 defining the surface $S_2$, is greater than in the embodiment of FIGS. 8 and 9, this making it possible to increase the effect of cant of the surface $S_2$ with respect to the rear face 426 if the base 421.

The components shown in FIGS. 8 to 11 may be considered as belonging to the same set of glenoidal components allowing the surgeon to select the component most adapted as a function of the value of the angle γ and of the orientation of the resectioned surface $S_G$ of the glenoidal cavity with respect to the longitudinal axis Z-Z' of the patient's spinal column.

Of course, the number of components of such a set is limited to two.

The characteristics of the different forms of embodiment shown may be combined together in that a base or plate with non-parallel front and rear faces might be used with an element provided with a skirt extending the portion of this element defining an axisymmetric convex articular surface.

The invention also allows a correct implantation of a glenoidal component when the lower part of the scapula is damaged. In that case, it suffices to turn the component with respect to the configuration shown in FIG. 2.

The invention has been shown with two-part glenoidal components. However, it is equally well applicable to one-piece glenoidal components.

What is claimed is:

1. A glenoid prosthesis comprising:
   a convex surface of articulation centered on an axis of symmetry;
   a base portion comprising a rear face configured to bear against the glenoid (G) when applied to the patient and a front face perpendicular to the axis of symmetry, the base portion configured to augment a degraded surface of the glenoid; and
   a stem comprising a first end extending from the rear face and a second end opposite the first end;
   wherein the axis of symmetry of the convex surface of articulation extends along a longitudinal axis through the first end and the second end of the stem;
   wherein the base portion is asymmetrical about the axis of symmetry of the convex surface; and
   wherein the axis of symmetry of the convex surface of articulation is not perpendicular to the rear face.

2. The glenoid prosthesis of claim 1, wherein the convex surface is disposed on an articular component, the articular component being mateable to the base portion.

3. The glenoid prosthesis of claim 2, wherein a non-zero angle is defined between the front face and the rear face.

4. The glenoid prosthesis of claim 2, wherein the articular component comprises a projection extending from a side opposite the convex surface and the base portion comprises a recess configured to receive the projection, wherein when the projection is received in the recess, the articular component is aligned to the basic portion.

5. The glenoid component of claim 4, wherein the projection comprises a finger.

6. The glenoid prosthesis of claim 1, wherein at least a portion of the rear face is not perpendicular to a longitudinal axis extending through the first end and the second end of the stem.

7. The glenoid prosthesis of claim 1, wherein the front face is perpendicular to a longitudinal axis extending through the first end and the second end of the stem.

8. The glenoid prosthesis of claim 1, wherein the rear face is substantially planar.

9. The glenoid prosthesis of claim 1, wherein the base portion comprises a wedge portion providing a larger rear-to-front distance at one area of the periphery of the glenoid component than at another area of the periphery spaced away from the wedge portion.

10. A glenoid prosthesis comprising:
    a glenoid component comprising:
      a base portion comprising a front face and a rear face configured to bear against the glenoid (G) when applied to the patient, and
      a stem extending from the rear face, the stem comprising a first end and a second end;
    an articular component being mateable to the glenoid component, the articular component comprising:
      a convex surface of articulation centered on an axis of symmetry, and
      a mating side disposed between the convex surface and the stem, wherein the axis of symmetry is perpendicular to the front face of the base portion and to a plane containing the mating side of the articular component, and
    wherein the axis of symmetry of the convex surface of articulation is not perpendicular to the rear face,
    wherein the base portion comprises a wedge portion configured to provide a larger rear-to-front distance at one area of a periphery of the glenoid component than at another area of the periphery spaced away from the wedge portion,
    wherein a longitudinal axis extending through the first end and the second end of the stem is non-perpendicular to at least a portion of the rear face forming the wedge portion; and
    wherein the axis of symmetry of the convex surface of articulation extends along the longitudinal axis through the first end and the second end of the stem.

11. The glenoid prosthesis of claim 10, wherein the convex surface forms a partial sphere.

12. The glenoid prosthesis of claim 10, wherein the mating side comprises a centering finger and the front face comprises a receptacle configured to receive the centering finger when the articular component is mated to the base portion.

13. The glenoid prosthesis of claim 12, wherein the receptacle extends from an opening on the front face toward the rear face of the base portion.

14. A glenoid prosthesis comprising:
- an articular component comprising a convex surface of articulation centered on an axis of symmetry, the articular component further comprising a projection extending from a side opposite the convex surface;
- a base portion comprising a rear face configured to bear against the glenoid (G) when applied to the patient, the base portion further comprising a recess configured to receive the projection; and
- a stem extending from a center of the rear face, the stem comprising a first end and a second end, wherein the axis of symmetry extends along a longitudinal axis through the first end and the second end of the stem;
- wherein the axis of symmetry of the convex surface of articulation is not perpendicular to the rear face, and
- wherein the base portion is asymmetrical about the axis of symmetry of the convex surface.

15. The glenoid prosthesis of claim 14, wherein the longitudinal axis extending through the first end and the second end of the stem is not perpendicular to at least a portion of the rear face.

* * * * *

UNITED STATES PATENT AND TRADEMARK OFFICE
CERTIFICATE OF CORRECTION

PATENT NO.        : 10,610,363 B2
APPLICATION NO.   : 15/379363
DATED             : April 7, 2020
INVENTOR(S)       : Alain Tornier et al.

It is certified that error appears in the above-identified patent and that said Letters Patent is hereby corrected as shown below:

On the Title Page

Column 1, Line 1, Item (72), under Inventors, delete "Saint Isnier" and insert --Saint Ismier--.

Column 1, Line 3, Item (72), under Inventors, delete "Lyons" and insert --Lyon--.

On Page 4, Column 2, Item (56), Other Publications, Line 31, delete "prosthese,"" and insert --prosthesis,"--.

In the Specification

In Column 1, Line 19, after "such a" delete "5".

In Column 2, Line 11, after "is" delete "20".

In Column 2, Lines 34-47, delete "glenoid cavity of a shoulder and.......of symmetry." and insert the same in Column 2, Line 33 as the continuation of same paragraph.

In Column 6, Line 53, delete "322a" and insert --$322_a$'--.

In the Claims

In Column 8, Line 19 (Approx.), Claim 4, delete "basic" and insert --base--.

In Column 8, Line 20, Claim 5, delete "component" and insert --prosthesis--.

In Column 8, Line 33, Claim 9, delete "the" and insert --a--.

In Column 8, Lines 33-34, Claim 9, delete "glenoid component" and insert --base portion--.

Signed and Sealed this
Eleventh Day of August, 2020

Andrei Iancu
*Director of the United States Patent and Trademark Office*